United States Patent [19]

Gristina

[11] 4,179,758

[45] Dec. 25, 1979

[54] FIXATION STEM FOR PROSTHETIC DEVICE

[75] Inventor: Anthony G. Gristina, Winston-Salem, N.C.

[73] Assignee: Howmedica, Inc., New York, N.Y.

[21] Appl. No.: 819,233

[22] Filed: Jul. 26, 1977

Related U.S. Application Data

[63] Continuation-in-part of Ser. No. 757,559, Jan. 7, 1977, Pat. No. 4,040,131, which is a continuation-in-part of Ser. No. 681,805, Apr. 29, 1976, Pat. No. 4,003,095.

[51] Int. Cl.² .................................................. A61F 1/24
[52] U.S. Cl. ...................................... 3/1.91; 128/92 C
[58] Field of Search .................................. 3/1.9–1.913; 128/92 C, 92 CA; 32/10 A

[56] References Cited

U.S. PATENT DOCUMENTS

| 3,715,763 | 2/1973 | Link | 3/1.911 |
| 3,849,888 | 11/1974 | Linkow | 32/10 A |
| 3,886,599 | 6/1975 | Schlein | 3/1.91 |
| 3,889,300 | 6/1975 | Smith | 3/1.91 |
| 4,021,864 | 5/1977 | Waugh | 3/1.91 |

FOREIGN PATENT DOCUMENTS

| 2408950 | 9/1975 | Fed. Rep. of Germany | 3/1.911 |
| 1362187 | 7/1974 | United Kingdom | 3/1.91 |

OTHER PUBLICATIONS

Oral Implantology, Book by Implants International–Oratronics, Inc., Suite 6100, The Chrysler Bldg., New York, N.Y. 10017, Copyright 1971, pp. 22–25.

*Primary Examiner*—Ronald L. Frinks
*Attorney, Agent, or Firm*—Connolly and Hutz

[57] ABSTRACT

Means for affixing the scapular component of a shoulder prosthesis to the bony structure of the shoulder includes a T-shaped stem extending from a flange on the device. The stem has a substantially narrow or thin web having one side longer than the other, which disposes the base at an acute angle relative to the flange, such as approximately 15°. The elongated base and the web are inserted through the bony structure with the flange in contact with outer regions. The base and web are cemented within the bone to securely anchor the prosthesis to the bone between them and the flange.

3 Claims, 11 Drawing Figures

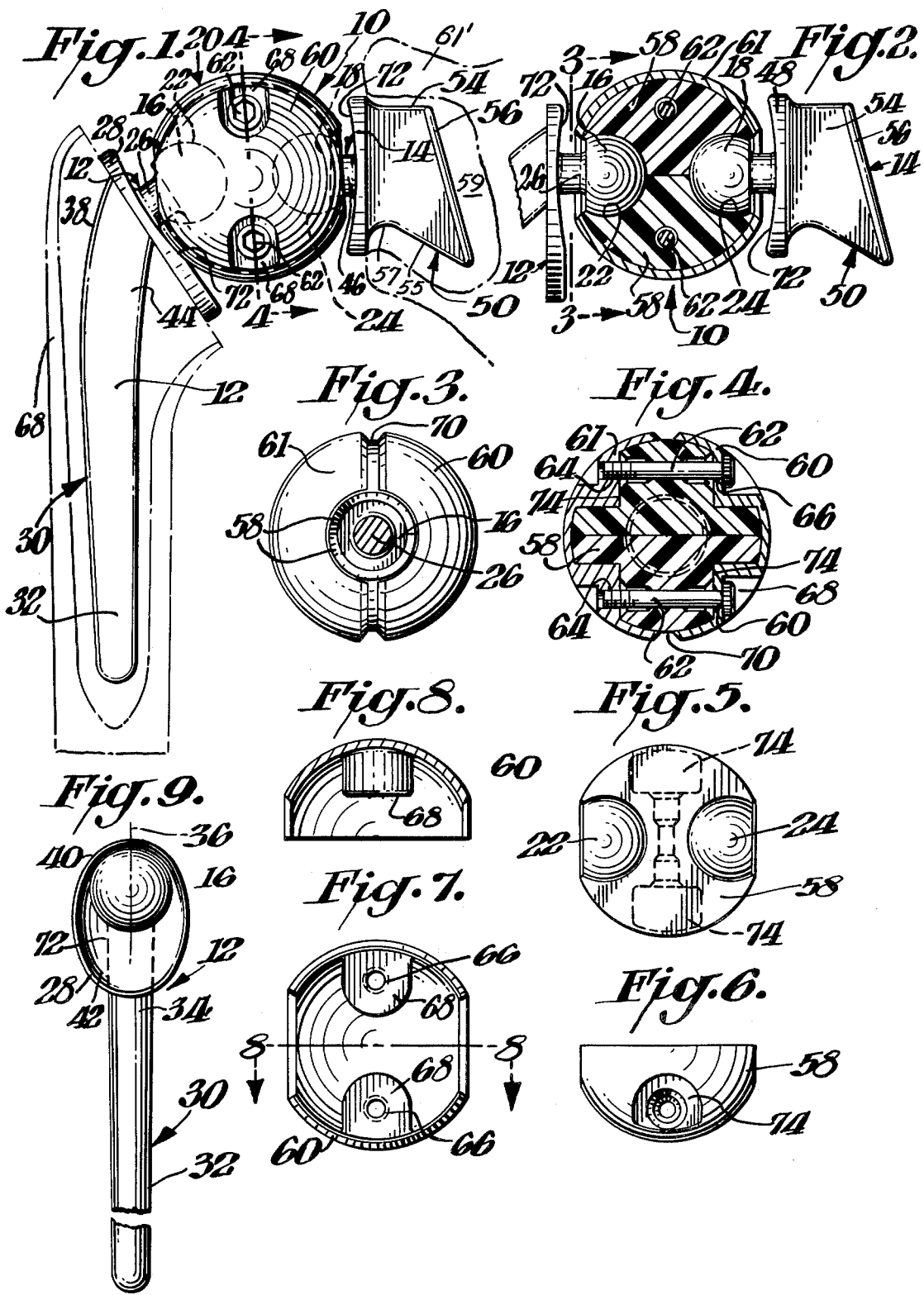

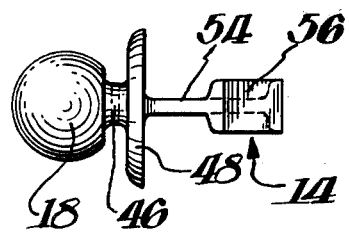
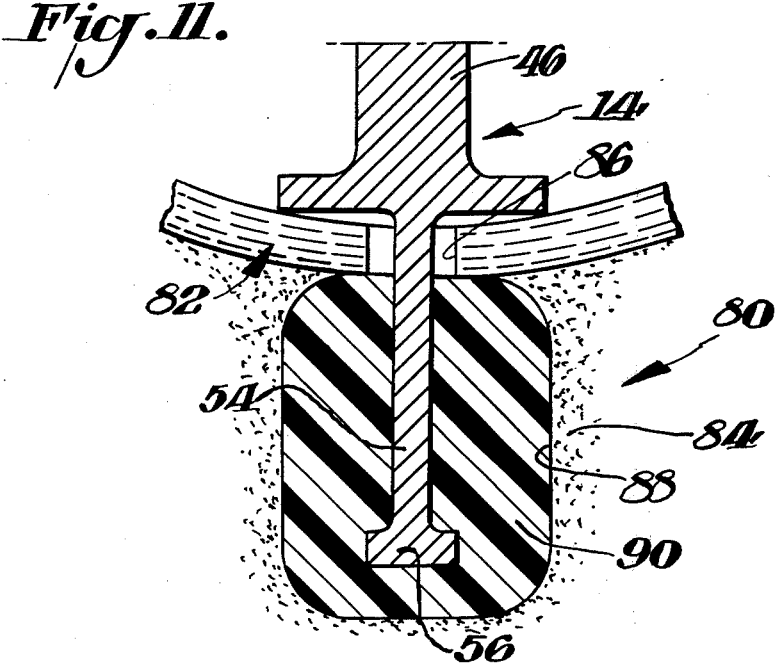

FIXATION STEM FOR PROSTHETIC DEVICE

CROSS REFERENCE TO RELATED APPLICATIONS

This application is a continuation-in-part of copending commonly assigned application Serial No. 757,559, filed Jan. 7, 1977, now U.S. Pat. No. 4,040,131 which in turn is a continuation-in-part of Serial No. 681,805, filed Apr. 29, 1976, which issued as U.S. Pat. 4,003,095 on Jan. 18, 1977 by this same inventor.

BACKGROUND OF THE INVENTION

Various prosthetic devices inserted within the human body must be firmly affixed to a bone or bony structure. An object of this invention is to provide a relatively simple and strong means for affixing a prosthetic device to the bony structure of the body. Another object is to provide such a means which is strong in tension, compression and shear.

SUMMARY

In accordance with this invention a means for affixing a component of a prosthetic device to bony structure in the body includes a T-shaped stem extending from a flange spaced from it on the device. The stem has a substantially narrow or thin web having one side longer than the other, which disposes the base at an acute angle relative to the flange, such as approximately 15°. The elongated base and the web are inserted through the bony structure to dispose the flange in contact with outer regions of the bone. The base and web are cemented within the bone to securely anchor the prosthesis to the bone by firmly gripping it between them and the flange.

BRIEF DESCRIPTION OF THE DRAWINGS

Novel features and advantages of the present invention will become apparent to one skilled in the art from a reading of the following description in conjunction with the accompanying drawings wherein similar reference characters refer to similar parts and in which:

FIG. 1 is a view in elevation of one embodiment of this invention on a prosthetic device for installation between the human shoulder and upper arm;

FIG. 2 is a partial view of the prosthesis shown in FIG. 1 in an articulated position;

FIG. 3 is a cross-sectional view taken through FIG. 2 along the line 3—3;

FIG. 4 is a cross-sectional view taken through FIG. 1 along the line 4—4;

FIG. 5 is an exterior plan view of one of the hemispherical plastic inserts used in the embodiment shown in FIGS. 1-4, with the other insert being a mirror image thereof;

FIG. 6 is an external elevational view of the insert shown in FIG. 5;

FIG. 7 is an internal plan view of the threaded retaining shell used in the embodiment shown in FIGS. 1-4 with the unthreaded shell substantially being a mirror image thereof;

FIG. 8 is a cross-sectional view taken through FIG. 7 along the line 8—8;

FIG. 9 is a front elevational view of the humeral component used in the embodiment shown in FIGS. 1-4;

FIG. 10 is a top plan view of the scapular component of the prosthesis shown in FIG. 1; and FIG. 11 is a schematic diagram of the manner in which the scapular component shown in FIG. 10 is affixed to the bony structure of the body.

DESCRIPTION OF THE PREFERRED EMBODIMENTS

In FIG. 1 is shown trispherical prosthetic shoulder device 10 including a humeral component 12 and a scapular component 14 having respectively a humeral ball 16 of relatively small diameter, such as about ½ inch or 12.5 mm and a scapular ball 18 of about the same diameter. Humeral ball 16 and scapular ball 18 are rotatably captured by a central spheroidal component or insert 20 about 1⅛ inches or 28.5 mm in diameter. Spherical sockets 22 and 24 in central component 20 rotatably capture slightly more than ½ of the spherical heads of balls 16 and 18 to securely rotatably capture them. Humeral component 12 also includes a neck 26 connecting ball 16 to flange 28 of substantially elliptical or oval shape (shown in FIG. 9). Ball 16 and neck 26 are eccentrically disposed approximately at one of the foci of elliptical flange 28. Stem 30 is connected to the other side of flange 28 and its slightly tapered end 32 is disposed at an angle of approximately 30° relative to flange 28. Neck 26 and ball 16 are disposed substantially perpendicularly to the other side of flange 28. The attached end 34 of stem 30 is slightly radially curved in planes parallel to the main axis 36 of flange 28, and has its convex surface 38 substantially contiguous to the outer edge 40 of the nearer end of flange 28. The other end 42 of flange 28 extends outwardly a considerable distance from the concave surface 44 of curved stem portion 34.

Humeral component 12 and scapular component 14 are made of biocompatible metal, such as, for example Vitallium. Vitallium ® is the trademark of Howmedica, Inc. for a special cobalt-chromium alloy developed and used for cast partial and full dentures and for internal applications by surgeons. Cobalt and chromium constitute over 90% of its composition. Vitallium is characterized by a specific gravity of 8.29; tensile strength, 95,000 lb.Sq.in. minimum; 2% offset yield strength, 65,000 lb./sq.in. minimum; reduction of area, 8% minimum; elongation, 8% minimum; and modulus of elasticity, 30,000,000–32,000,000 lb./sq.in. When polished, it is exceedingly smooth and permanently lustrous. Its outstanding qualities are clinical inertness in relation to living tissues and high degree of resistance to corrosion.

As shown in FIGS. 2 and 10, scapular component 14 has a neck 46 joining ball 18 to substantially the center of elliptical flange 48, in a substantially perpendicular disposition. T-shaped affixation stem 50 is joined to the other side of flange 48. Stem 50 includes a substantially narrow web 54 joining elongated base 56 to flange 48. Web 54 is longer at one end than the other and thus disposes base 56 at an acute angle relative to flange 48, such as approximately 15°. End 55 is cutout at 57 facilitating insertion in undercut opening 59 in bony structure 61'. Scapular stem 50 and humeral stem 30 are both cemented in place by a suitable bone cement, such as methyl methacrylate.

Central component 20 includes a pair of plastic cutout hemispheres of biocompatible plastic 58, shown in FIGS. 2, 3, and 4 sharing spherical sockets 22 and 24 of a slightly greater than radial depth for capturing balls 16 and 18. Hemispheres 58 are, for example, made of high density or ultra-high density polyethylene. They are joined securely together about balls 16 and 18 by a pair of hemispherical shells 60, 61 and hexagonal headed cap screws 62 engaged in threaded sockets 64 in shell 61 and passing through smooth socket 66 in shell 60. Shells 60 and 61 and screws 62 are also made of Vitallium, for example. Sockets 64 and 66 and the heads of cap screws 62 are secured within indentations 69 in shells 60 and 61. Indentations 69 in shells 60 and 61 are received in mating indentations 74 in hemispherical inserts 58.

FIGS. 1 and 2 show various articulated positions of shoulder prosthesis 10. In FIG. 1, humeral component 12 and human arm 68 are disposed in a substantially downwardly extending vertical position with the inward motion of humeral component 12 arrested by contact of neck 26 on the lower edge of socket 22.

FIG. 2 shows a somewhat raised position of prosthesis 10 in which ball 16 of central component 20 has rotated upwardly within socket 22 to approximately 30° from the position shown in FIG. 1.

FIG. 3 shows narrow space 70 between shells 60 and 61 when they are secured together. This space insures firm engagement of plastic inserts 58 together about balls 16 and 18. Due to overlap or extension of plastic shown in FIG. 1 beyond equator of spherical heads, there is provided total retention of all of the ball components within plastic inserts 58. Also, total capture of parts 10 provided since the opening in the metal shell is less than the diameter of the spherical heads.

At extreme end of motion contact occurs between the outer surface 72 of the flanges 28 and 48 and the outside surfaces of the metal shells 60 and 61. This distributes the load over a greater area which reduces impact stresses. Many current designs allow contact of the neck with the thin edge of the mating part. This arrangement can lead to deformation of contacting surfaces due to the high bearing stresses which can occur.

During end of allowable range of motion the parts cannot "cam-out". Either implantable component will rotate around instant center producing rotational vector which is directed into the plastic and surrounding metal shell. This means that in order for dislocation to occur the spherical head must completely deform plastic and product local yielding of the shell—which is a very unlikely possibility.

FIG. 11 shows scapular component 14 affixed to bony structure 80 of the human body, such as to the scapular bony region 80 of the body, including a subchondral plate 82 with cancellous bone matter 84 disposed within it.

The bone 82 is prepared in a special manner consisting of cutting a small key-hole slot 86, in the subchondral plate 82. The major portion of the strong subchondral bone structure is preserved. Cavity 88 of the underlying cancellous bone is removed with an undercutting beneath the retained subchondral plate 82. The cavity 88 is filled with cement 90, such as Simplex cement and the fixation stem 50 is inserted.

Simplex ® is the trademark for a bone cement sold by Howmedica Inc. of the methyl methacrylate type. Any suitable bone cement may also be utilized.

Invitro testing, using cadaveric bone specimens has shown that the proposed fixation stem design exhibits levels of strength (tension, compression, and shear) that exceed that of the anatomic joint subjected to normal clinical use. The T-shaped fixation stem functions to key-in the mantle of cement and distributes the forces to the subchondral plate during periods of imposed loading of the implanted component.

I claim:

1. A movable prosthetic device adapted for affixation to bony structure having a relatively strong bone plate like region comprising a substantially T-shaped stem, a substantially elongated base incorporated in the stem, a substantially narrow web incorporated in the stem connecting the substantially elongated base to the device, a flange on the device which is spaced from the base of the stem is adapted to be affixed to the bony structure by insertion of the base and web through a hole in the bone plate and into a mass of cement disposed under the bone plate with the flange disposed in firm contact with the outside of the bone plate, the base is substantially flat, the base is disposed at an acute angle relative to the flange, the flange is substantially oval, the web has longer and shorter sides, and a portion of the longer side disposed adjacent the flange has a cutout to facilitate insertion of the base through the hole in the bone plate.

2. A device as set forth in claim 1 wherein the acute angle is about 15°.

3. A prosthetic device which is adapted for affixation to bony structure having a relatively strong bone plate-like region comprising a flange, the device being attached to one side of the flange, a thin quadrilateral web projecting essentially at right angles from the other side of the flange, the web having length along the flange, the web having height disposed substantially perpendicular to the flange, the web length being greater than the web height; an elongated base having a greater width than the web disposed along the opposite side of the web from the flange, the web and base comprising a stem of T-shaped cross section in which the base width comprising a T crossbar is substantially shorter than the web height which comprises a T staff, and the base and web having a thickness which is approximately the same and which is substantially thinner than the base width whereby the stem is adapted to be cemented under the bony plate-like region with the flange disposed upon the region and with the web extending through a hole in the region to affix the device to the bony structure.

* * * * *